(12) United States Patent
Fritzsch et al.

(10) Patent No.: US 10,486,165 B2
(45) Date of Patent: Nov. 26, 2019

(54) REFILLABLE COLUMN SYSTEM

(71) Applicant: Miltenyi Biotec GmbH, Bergisch Gladbach (DE)

(72) Inventors: Frederik Fritzsch, Köln (DE); Philipp Steinbrück, Bergisch Gladbach (DE); Oliver Schilling, Bergisch Gladbach (DE); Ursula Bissa, Leverkusen (DE)

(73) Assignee: Miltengi Biotec, GmbH, Bergisch Gladbach (DE)

( * ) Notice: Subject to any disclaimer, the term of this patent is extended or adjusted under 35 U.S.C. 154(b) by 97 days.

(21) Appl. No.: 15/952,524

(22) Filed: Apr. 13, 2018

(65) Prior Publication Data

US 2018/0326429 A1  Nov. 15, 2018

(30) Foreign Application Priority Data

May 9, 2017  (EP) .................................. 17170065

(51) Int. Cl.
*B03C 1/034* (2006.01)
*B01L 3/00* (2006.01)
*B03C 1/01* (2006.01)

(52) U.S. Cl.
CPC ........ *B03C 1/034* (2013.01); *B01L 3/502753* (2013.01); *B03C 1/01* (2013.01); *B01L 2200/0652* (2013.01); *B01L 2200/0689* (2013.01); *B01L 2300/041* (2013.01); *B01L 2300/048* (2013.01); *B01L 2300/0681* (2013.01); *B01L 2400/04* (2013.01); *B01L 2400/043* (2013.01); *B03C 2201/18* (2013.01)

(58) Field of Classification Search
CPC .......... B03C 1/034; B03C 1/01; B03C 1/032; B03C 1/031; B03C 1/029; B01L 3/502753; B01L 3/502
See application file for complete search history.

(56) References Cited

U.S. PATENT DOCUMENTS

| | | | | |
|---|---|---|---|---|
| 2,799,981 A | * | 7/1957 | Baker-Carr | B29C 65/00 53/478 |
| 3,255,752 A | * | 6/1966 | Dick | A61M 5/284 604/89 |
| 3,757,779 A | * | 9/1973 | Rovinski | A61M 5/284 604/190 |
| 4,070,249 A | | 1/1978 | Janin | |
| 5,385,707 A | | 1/1995 | Miltenyi | |
| 5,693,539 A | | 12/1997 | Miltenyi | |
| 6,602,422 B1 | | 8/2003 | Miltenyi | |
| 2006/0079834 A1 | | 4/2006 | Tennican | |

* cited by examiner

*Primary Examiner* — Chester T Barry
(74) *Attorney, Agent, or Firm* — Jaquelin K. Spong

(57) ABSTRACT

The invention is directed to a column system for separation of particles comprising a reservoir section with a input opening; a filter section provided with a filter matrix and an output opening and a plunger having a first and a second end, the first end fitting into the reservoir section characterized in that the plunger is provided with at least one channel providing gaseous communication from the first end to the second end. The column system may be used for magnetic cell separation.

9 Claims, 3 Drawing Sheets ional patent application claims priority to European Patent Application Serial No. EP17170065.1, filed May 9, 2017.

STATEMENT REGARDING FEDERALLY SPONSORED RESEARCH

Not applicable.

STATEMENT REGARDING MICROFICHE APPENDIX

Not applicable.

BACKGROUND

The present invention is directed to a column system for separation of particles, especially for magnetic separation of cells.

Magnetic cell separation is an established technology to separate magnetically labelled cells from non-magnetic cells by utilizing a high gradient magnetic field in which the magnetically labelled target cells are retained. Usually, a suspension of magnetically labelled cells and non-magnetic cells are guided through a column provided with a ferromagnetic matrix, which is subjected to a strong magnetic field. The magnetically labelled cells are retained on the ferromagnetic matrix, whereas the non-magnetic cells are eluted. The magnetically labelled cells may then be harvested by removing the column from the magnetic field and rinsing the cells from the matrix. This technology is for example described in U.S. Pat. Nos. 5,693,539 or 5,385,707.

The separation process is usually performed without applying pressure i.e. under normal gravity conditions, but enhanced pressure may be applied to speed up the process or to reduce the volume of the liquid. In this respect, U.S. Pat. No. 6,602,422 discloses a micro column system for magnetic cell separation provided with a plunger, which can be used to apply pressure in order to flush out liquid from the column.

In theory, such columns for magnetic cell separation can be used for several subsequent separation processes. However, most columns for magnetic cell separation are provided with a ferromagnetic matrix like a ferromagnetic mesh, steel wool, wire wool, wire sponge or ferromagnetic particles. If the liquid is removed from the matrix, for example by draining, air becomes entrapped in the ferromagnetic matrix. Due to the porous nature of the matrix, entrapped air can hardly be removed and blocks the matrix at least in part for further liquid. This results in a reduced separation speed, in worst case in a total stop of the separation process.

The plunger as disclosed in U.S. Pat. No. 6,602,422 might be used to force liquid (and entrapped air) through and out of the matrix, but by removing the plunger to add additional liquid, air is again sucked into the matrix, this time from the exit port of the column. In other words, the column described in U.S. Pat. No. 6,602,422 is not suitable for reuse, even with using the plunger.

SUMMARY

Accordingly, it was the object of the invention to provide a column system for magnetic particle separation to which pressure or vacuum may applied without the danger of sucking or pressing air into the ferromagnetic matrix.

Object of the invention is therefore a column system for separation of particles comprising a reservoir section with a input opening; a filter section provided with a filter matrix and an output opening and a plunger having a first and a second end, the first end fitting into the reservoir section characterized in that the plunger is provided with at least one channel providing gaseous communication from the first end to the second end.

Although the channel may be opened or closed with a finger of the person using the column, for convenience or safety, the channel may be provided at the second end with a closing means like a flip-cap, a screw cap or an adhesive film as shown in FIG. 1 or 2

A further object of the invention is a process for separation of particles is a column comprising a reservoir section with a input opening; a filter section provided with a filter matrix and an output opening and a plunger having a first and a second end, the first end fitting into the reservoir section wherein the plunger is provided with at least one channel providing gaseous communication from the first end to the second end and with a closing means for the channel located at the second end wherein a suspension of particles is provided to the reservoir section; the first end of the plunger is inserted into the input opening of the column section with the closing means being closed; the plunger is moved towards the filter matrix thereby pressing the suspension through the filter matrix; opening the closing means and removing the plunger from the column.

Opening or closing the channel may be performed with a finger of the operating person. In alternative, the channel is opened or closed with a closing means provided at the second end of the plunger.

DETAILED DESCRIPTION

The column system of the invention comprises two separate objects: first, the column itself, comprising a reservoir section (11) with an input opening (12); a filter section (13) provided with a filter matrix and an output opening (14) and second, the plunger.

In the following, the term "plunger" refers to any object like a piston, which can be inserted in a water-tight fashion in the reservoir section of the column.

Plunger

Figure 1:
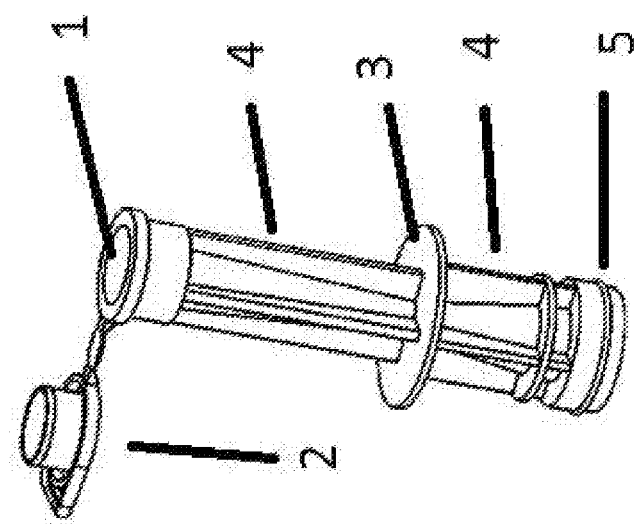
FIG. 1 shows the plunger of the invention with (1) channel, (2) closing means, (3) distance piece (spacer), (4) stabilizer means, (5) sealing means.
Figure 2:
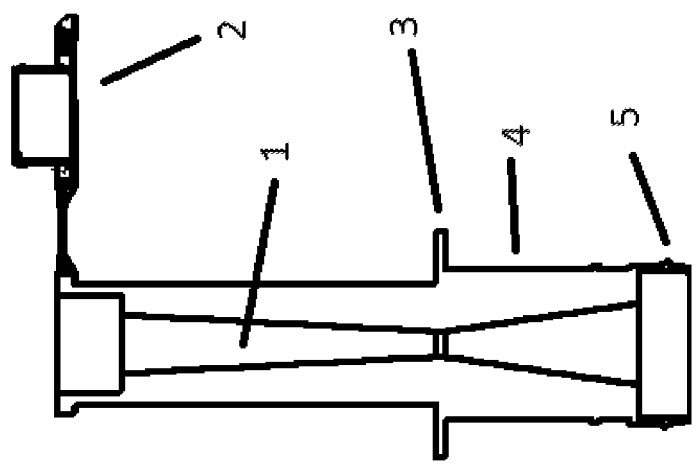
FIG. 2 is a side view of the plunger of the invention with (1) channel, (2) closing means, (3) distance piece (spacer), (4) stabilizer means, (5) sealing means.

In a first embodiment, the plunger is provided at the second end with a closing means (2) for the channel as shown in FIGS. 1 and 2. Suitable as closing means (2) are for example a flip-cap, a screw cap or an adhesive film.

In a second embodiment, the plunger is provided with a means (3) to adjust the distance to which the first end of the plunger is inserted into the reservoir section. The distance holder may be a circular plate ((3) in FIGS. 1 and 2) or any object extending from the plunger body far enough to prevent the plunger from being inserted too deeply into the reservoir.

The spacer means or distance holder shall be located at a position at least to prevent the plunger from reaching or touching the matrix. This ensures that the matrix is covered with liquid at any time and no air is introduced into the matrix. Preferable, the plunger is provided with a spacer means at a position to prevent the plunger from being inserted into the reservoir to more than 90%, preferable more than 75% and most preferred more than 60% of the total volume of the reservoir. Accordingly, even with the plunger inserted in the reservoir, the matrix would still be covered by liquid filling up to 10%, 25% or 40% of the volume of the reservoir.

In another embodiment, the plunger is provided with stabilizer means (4) fitting into the reservoir section. The stabilizer means are shown as (4) in FIGS. 1 and 2 and may be provided as fins or stretched walls located around the channel of the plunger extending from the first to the second end of the plunger. The stabilizer means shall prevent torsion of the plunger and/or enable mechanical pressure being applied to any liquid in the reservoir.

The plunger, distance holder (3) and stabilizer means (4) are preferable produced from the same material as monolithic object.

The channel (1) of the plunger may have any volume, shape or internal diameter as long as it is sufficient to transport air from the reservoir to the outside of the system (i.e. to serve as a pressure compensation). In a preferred version shown in FIG. 2, the channel is double-cone shaped (hourglass shape) to provide additional mechanical stability to the plunger.

The plunger may be provided with a sealing or gasket (5) like an O-ring at the first end. Plungers without sealing should have an outer diameter at the first end slightly larger than the inner diameter of the reservoir, like a plunger in a common disposable syringe. Plungers with a sealing should have an outer diameter at the first end slightly smaller or identical to the inner diameter of the reservoir.

Column

The column itself comprises a reservoir section with an input opening; a filter section provided with a filter matrix and an output opening. As long as the plunger fits in a water tight fashion into the reservoir section, the shape or volume of the column has little effect to the invention. Suitable columns are for example disclosed in U.S. Pat. No. 6,602,422 and/or are available from Miltenyi Biotec GmbH under the tradename "MACS column".

The column is preferably made of plastics such as polyamide, polystyrene, polyolefin like polyethylene and polypropylene, polycarbonate, polyoxymethylene, acrylics, like polymethylmethacrylate, PET, poly lactic acid, polyamides or steel, and the like. When the matrix is coated with lacquer, is preferably made of a plastic that will bind with lacquer, most preferably a resin such as PCTG (polycyclohexadimethylterephtalate modified with ethylenglycol). The column may be made hydrophilic by manufacturing it from a hydrophilic material such as a hydrophilic plastic, or, more preferably, by coating the inside of the column with a hydrophilic material, e.g., polyvinyl pyrrolidone.

The column system according to the invention is provided with a filter matrix, preferable with a ferromagnetic matrix. In such ferromagnetic matrix, a high gradient magnetic field may be generated by insertion of at least the part of the column where the ferromagnetic matrix is located into an external magnetic field. The ferromagnetic matrix readily demagnetizes when it is taken out of the field.

The external magnetic field may be provided by a magnetic yoke or an electromagnet, which should provide a magnetic field greater than about 0.2 Tesla.

Preferably, the column system of the present invention is designed to operate by gravity feed, but may alternatively be operated under a pressure feed. To permit this, the plunger fits into the reservoir and can be used to flush the column/matrix with liquid.

A porous frit or grid may be positioned adjacent the top end of the matrix. The porous frit/grid is preferably made of glass or plastic or metal mesh and has a pore size greater than or equal to the pore size of the matrix and less than the particle size of the matrix.

The ferromagnetic material may comprise ferromagnetic balls or other ferromagnetic particles. The ferromagnetic material may be coated with a coating which maintains the relative position of the particles with respect to one another. The ferromagnetic balls or particles preferably have a diameter or size of at least 100 µm, more preferably greater than about 200 µm and less than about 2000 µm, still more preferably greater than about 200 µm and less than about 1000 µm, and most preferably about 280 µm.

Process of Manufacture of the Device

The device of the invention may be manufactured by any method known to a person skilled in the art. Preferred methods are injection molding and 3D printing, for example by extrusion deposition, fused deposition modeling, stereo lithography or photopolymer digital light processing.

A person skilled in the art is familiar with such 3D printing processes and the necessary equipment. A suitable 3D printer is for example M120 Scan-LED Printer from Innovation MediTech GmbH, with FotoMed® LED.A as printing photoresist polymer. Usually, layers of polymer having a thickness of 25 µm are cured by UV radiation with subsequent removal of the liquid uncured FotoMed® LED.A. by shaking. After the final layer is printed/cured, the uncured FotoMed® LED.A is removed by flushing the object in ultrasonic bath filled with isopropanol. Finally, post curing in $N_2$ atmosphere e.g. in the post curing unit PCU 90 (Innovation MediTech GmbH) may be performed.

Use of the Device

In general, the process of the invention is directed to separate particles. In particular, the process is directed to separation of cells (i.e. the particles are cells) and the separation is conducted by magnetically labeling the cells, and withholding the magnetically labeled cells in the matrix by placing the column in a magnetic field.

Accordingly, in a preferred embodiment, the filter matrix is a ferromagnetic matrix and the process is performed at least in part by placing the filter section of the column in a magnetic field.

Various techniques of magnetically labeling cells are known in the art for more than 20 years. Common to these processes is the selective magnetically labeling of cells via antibodies conjugated to magnetic particles, introduction of the cells as suspension to a column placed in a strong magnetic field and retaining the labeled cells on the matrix. To obtain the magnetic labeled cells from the column after separation, the matrix is usually flushed with buffer and as a result of this, air is also flushed into the matrix. Due to the air in the matrix, the column is not functional anymore and it is not possible to reuse it for further separations.

Figure 3:
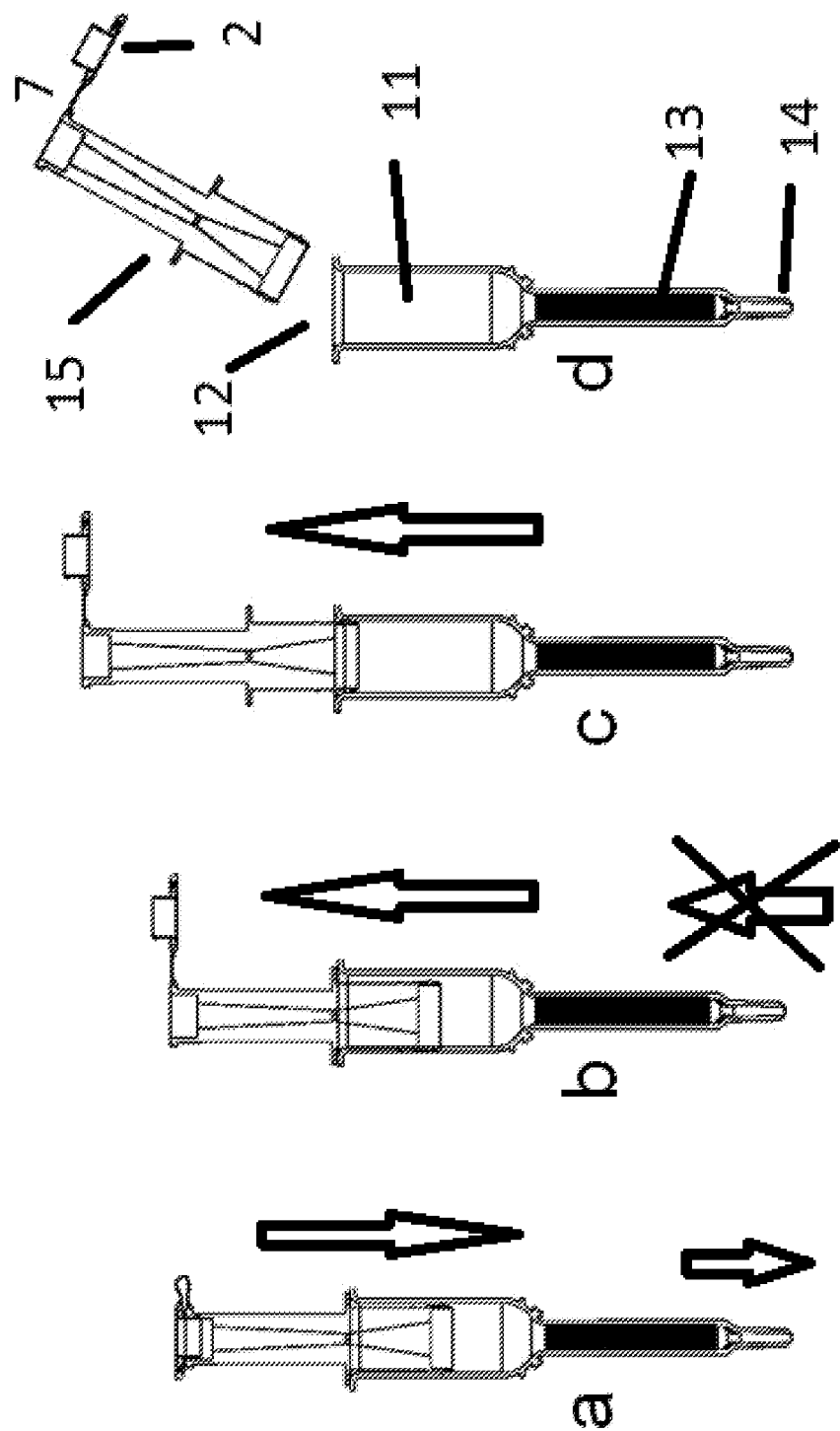
FIG. 3 show the column of the invention in use.

With the column of the invention, it is possible to elute the target material without flushing the column with air. The process of the invention is indicated in FIG. 3, where buffer is added to the column and by pushing the plunger with the cap closed into the column, target material is eluted from the column, but the matrix is still covered with liquid like buffer.

The spacer prevents insertion of the plunger too deep into the reservoir (a). Then, by opening the closing means (b), the plunger can be removed from the reservoir without sucking air into the matrix of the column through the outlet (c/d). The matrix does not contain any entrapped air, is still wetted and may be used for a further separation process.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A column system for separation of particles comprising:
    a reservoir section with an input opening;
    a filter section provided with a filter matrix and an output opening, wherein the filter matrix is a ferromagnetic matrix; and
    a plunger having a first and a second end, the first end fitting into the reservoir section wherein the plunger is provided with at least one channel providing gaseous communication from the first end to the second end.

2. The column system according to claim 1, wherein the channel is provided at the second end with a closing means.

3. The column system according to claim 1, wherein the plunger is provided with a means to adjust the distance to which the first end of the plunger is inserted into the reservoir section.

4. The column system according to claim 1, wherein the plunger is provided with stabilizer means fitting into the reservoir section.

5. The column system according to claim 1, wherein the plunger is provided with a sealing means at first end.

6. The column system according to claim 1, wherein the plunger is provided with a flip-cap, a screw cap or an adhesive film as closing means.

7. A process for separation of particles using a column comprising a reservoir section with a input opening; a filter section provided with a filter matrix and an output opening and a plunger having a first and a second end, the first end fitting into the reservoir section wherein the plunger is provided with at least one channel providing gaseous communication from the first end to the second end, comprising:
    providing a suspension of particles to the reservoir section;
    inserting the first end of the plunger into the input opening of the column section with the channel being closed;
    moving the plunger towards the filter matrix thereby pressing the suspension through the filter matrix; and
    opening the channel and removing the plunger from the column.

8. The process according to claim 7, wherein the channel is opened or closed with a closing means provided at the second end of the plunger.

9. The process according to claim 7, wherein the filter matrix is a ferromagnetic matrix and the process is performed at least in part by placing the filter section of the column in a magnetic field.

* * * * *